(12) United States Patent
Meree et al.

(10) Patent No.: US 11,173,069 B2
(45) Date of Patent: Nov. 16, 2021

(54) EARPLUG WITH STEM COMPRISING A SLEEVE

(71) Applicant: 3M INNOVATIVE PROPERTIES COMPANY, St. Paul, MN (US)

(72) Inventors: Caitlin E. Meree, St. Paul, MN (US); James P. Endle, New Richmond, WI (US); Joshua M. Fishman, Minneapolis, MN (US); Hannah L. Mathers, St. Paul, MN (US); Travis L. Potts, Woodbury, MN (US); Joseph D. Rule, Woodbury, MN (US); Richard J. Webb, St. Paul, MN (US); Caroline M. Ylitalo, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 216 days.

(21) Appl. No.: 16/471,844

(22) PCT Filed: Dec. 14, 2017

(86) PCT No.: PCT/US2017/066439
§ 371 (c)(1),
(2) Date: Jun. 20, 2019

(87) PCT Pub. No.: WO2018/118647
PCT Pub. Date: Jun. 28, 2018

(65) Prior Publication Data
US 2020/0100942 A1     Apr. 2, 2020

Related U.S. Application Data

(60) Provisional application No. 62/437,383, filed on Dec. 21, 2016.

(51) Int. Cl.
*A61F 11/08* (2006.01)

(52) U.S. Cl.
CPC .................................... *A61F 11/08* (2013.01)

(58) Field of Classification Search
CPC .... A61F 11/08; A61F 11/06; A61F 2011/085; A61F 11/10; A61F 11/12; A61F 11/14; H04R 25/02
(Continued)

(56) References Cited

U.S. PATENT DOCUMENTS 3,301,253 A    1/1967   Glorig
4,158,087 A    6/1979   Wood
(Continued)

FOREIGN PATENT DOCUMENTS

DE    102004051177    5/2005
GB        438283     11/1935
(Continued)

OTHER PUBLICATIONS

International Search Report for PCT International Application No. PCT/US2017/066439, dated Apr. 10, 2018, 6 pages.

*Primary Examiner* — Camtu T Nguyen
(74) *Attorney, Agent, or Firm* — Kenneth B. Wood (57) ABSTRACT

A hearing-protective earplug (1) with a resilient polymeric foam body (10) and with a grippable stem (110) that includes a forward portion (111) with an annular sleeve (112) that at least partially defines an open-ended, front-facing cavity (114) within which a rearward portion (21) of the resilient polymeric foam body resides.

15 Claims, 7 Drawing Sheets

(58) Field of Classification Search
USPC .......... 128/864, 866–868; 181/128–131, 181/134–135
See application file for complete search history.

(56) References Cited

U.S. PATENT DOCUMENTS

| | | | |
|---|---|---|---|
| 4,434,794 A | 3/1984 | Leight | |
| 4,724,922 A | 2/1988 | Kalayjian | |
| 5,188,123 A | 2/1993 | Gardner, Jr. | |
| 5,203,352 A | 4/1993 | Gardner, Jr. | |
| 5,573,015 A | 11/1996 | Williams | |
| 5,650,450 A | 7/1997 | Lovette | |
| 5,792,998 A | 8/1998 | Gardner, Jr. | |
| 5,799,658 A | 9/1998 | Falco | |
| 5,811,742 A | 9/1998 | Leight | |
| 5,988,313 A | 11/1999 | Hakansson | |
| 6,006,857 A | 12/1999 | Leight | |
| 6,241,042 B1 | 6/2001 | Falco | |
| 6,345,684 B1 | 2/2002 | Leight | |
| 6,568,395 B2 | 5/2003 | Tiemens | |
| 6,586,483 B2 | 7/2003 | Kolb | |
| 6,659,103 B2 | 12/2003 | Tiemens | |
| 6,695,093 B1 | 2/2004 | Falco | |
| 6,938,622 B2* | 9/2005 | Huang | A61F 11/12 128/864 |
| 7,096,872 B2 | 8/2006 | Ligon, Sr. | |
| 7,192,544 B2 | 3/2007 | Jenkins, Jr. | |
| 7,220,372 B2 | 5/2007 | Woo | |
| 7,285,576 B2 | 10/2007 | Hyde | |
| 7,464,786 B2 | 12/2008 | Falco | |
| 7,475,686 B2 | 1/2009 | Knauer | |
| 7,510,046 B2 | 3/2009 | Doty | |
| 7,727,433 B2 | 6/2010 | Knauer | |
| 7,731,487 B2 | 6/2010 | Knauer | |
| 7,837,005 B2 | 11/2010 | Killion | |
| 8,061,472 B2 | 11/2011 | Tiemens | |
| 8,161,975 B2 | 4/2012 | Turdjian | |
| 8,413,663 B2 | 4/2013 | Turdjian | |
| 8,679,607 B2 | 3/2014 | Hamer | |
| 9,814,625 B2* | 11/2017 | Ely | A61F 11/12 |
| 2003/0029460 A1 | 2/2003 | Tiemens | |
| 2008/0264429 A1 | 10/2008 | Leong | |
| 2010/0300460 A1 | 12/2010 | Falco | |
| 2010/0307861 A1 | 12/2010 | Tiemens | |
| 2012/0272974 A1 | 11/2012 | Magidson | |

FOREIGN PATENT DOCUMENTS

| | | |
|---|---|---|
| TW | 200918026 | 5/2009 |
| WO | WO 1992-014427 | 9/1992 |
| WO | WO 2009-001231 | 12/2008 |
| WO | WO 2014-011412 | 1/2014 |
| WO | WO 2017-222891 | 12/2017 |

* cited by examiner

EARPLUG WITH STEM COMPRISING A SLEEVE

BACKGROUND

Hearing-protective earplugs are well known. Compressible or "roll-down" type earplugs generally comprise a compressible, resilient sound-attenuating body made of a suitable slow recovery foam material. The body may be positioned at least partially within the ear canal of a user by rolling it between fingers to compress the body, then inserting the body into the ear canal, and subsequently allowing the body to expand to fill the ear canal. Push-in type earplugs generally include a relatively soft and resilient sound-attenuating body and a stem that extends rearwardly from the attenuating body. To insert a push-in type earplug, the user grasps the stem and uses it to push the sound-attenuating portion at least partially into the ear canal.

SUMMARY

In broad summary, herein is disclosed a hearing-protective earplug comprising a resilient polymeric foam body and comprising a grippable stem that comprises a forward portion with an annular sleeve that at least partially defines an open-ended, front-facing cavity within which a rearward portion of the resilient polymeric foam body resides. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted.

Terms such as forward, forwardmost, front, and the like, as used in characterizing features of an earplug, refer to a direction that is toward the interior of the ear canal (i.e. toward the sagittal plane of the user's head) when the earplug is inserted into the ear canal. Terms such as rearward, rearmost, and the like, refer to an opposite direction that is outward, away from the interior of the ear canal and away from the sagittal plane of the user's head. Terms such as radially-inward, radially-outward, and the like, respectively denote inward and outward directions with reference to a centerline extending along the long axis of the earplug.

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties; within +/−30 degrees for angular orientations). The term "substantially", unless otherwise specifically defined, means to a high degree of approximation (e.g., within +/−10% for quantifiable properties; within +/−15 degrees for angular orientations). The term "essentially" means to a very high degree of approximation (e.g., within +/−2% for quantifiable properties; within +/−5 degrees for angular orientations); it will be understood that the phrase "at least essentially" subsumes the specific case of an "exact" match. However, even an "exact" match, or any other characterization using terms such as e.g. same, equal, identical, uniform, constant, and the like, will be understood to be within the usual tolerances or measuring error applicable to the particular circumstance rather than requiring absolute precision or a perfect match. All references herein to numerical parameters (dimensions, ratios, and so on) are understood to be calculable (unless otherwise noted) by the use of average values derived from a number of measurements of the parameter.

DETAILED DESCRIPTION

Figure 1:
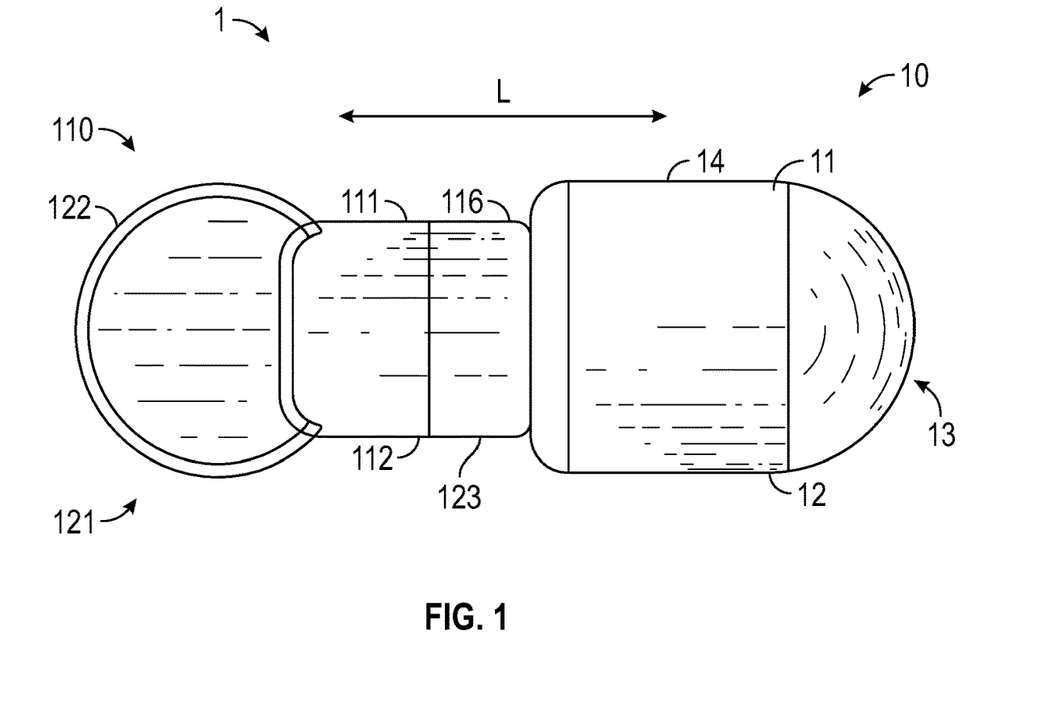
FIG. 1 is a side view of an exemplary earplug as disclosed herein.
Figure 2:
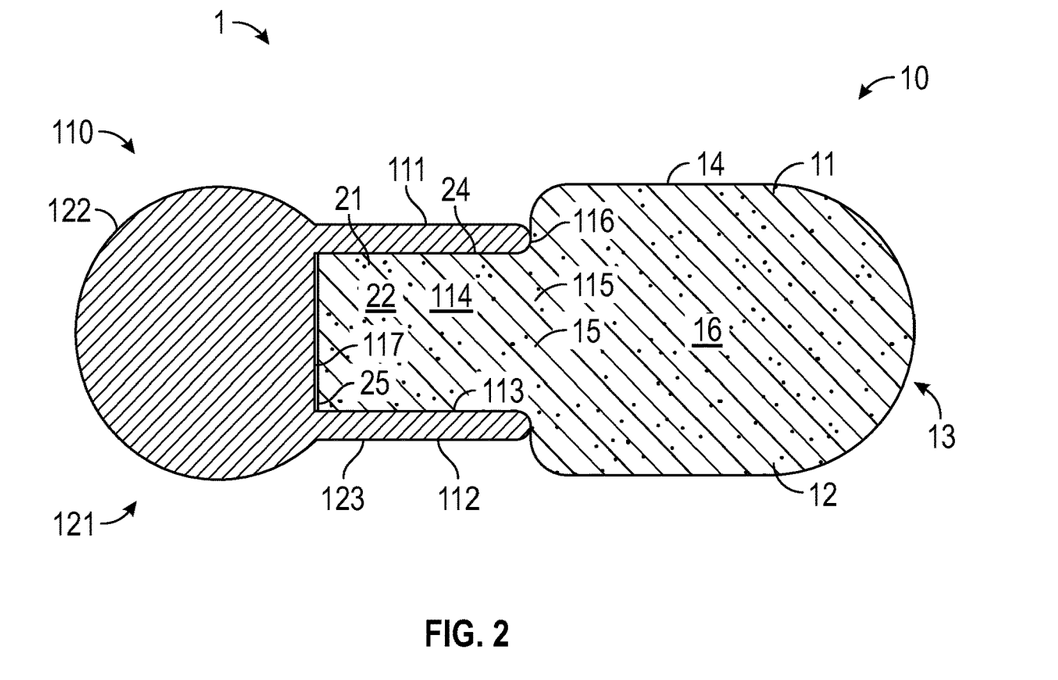
FIG. 2 is a side schematic cross-sectional view of the exemplary earplug of FIG. 1.
Figure 3:
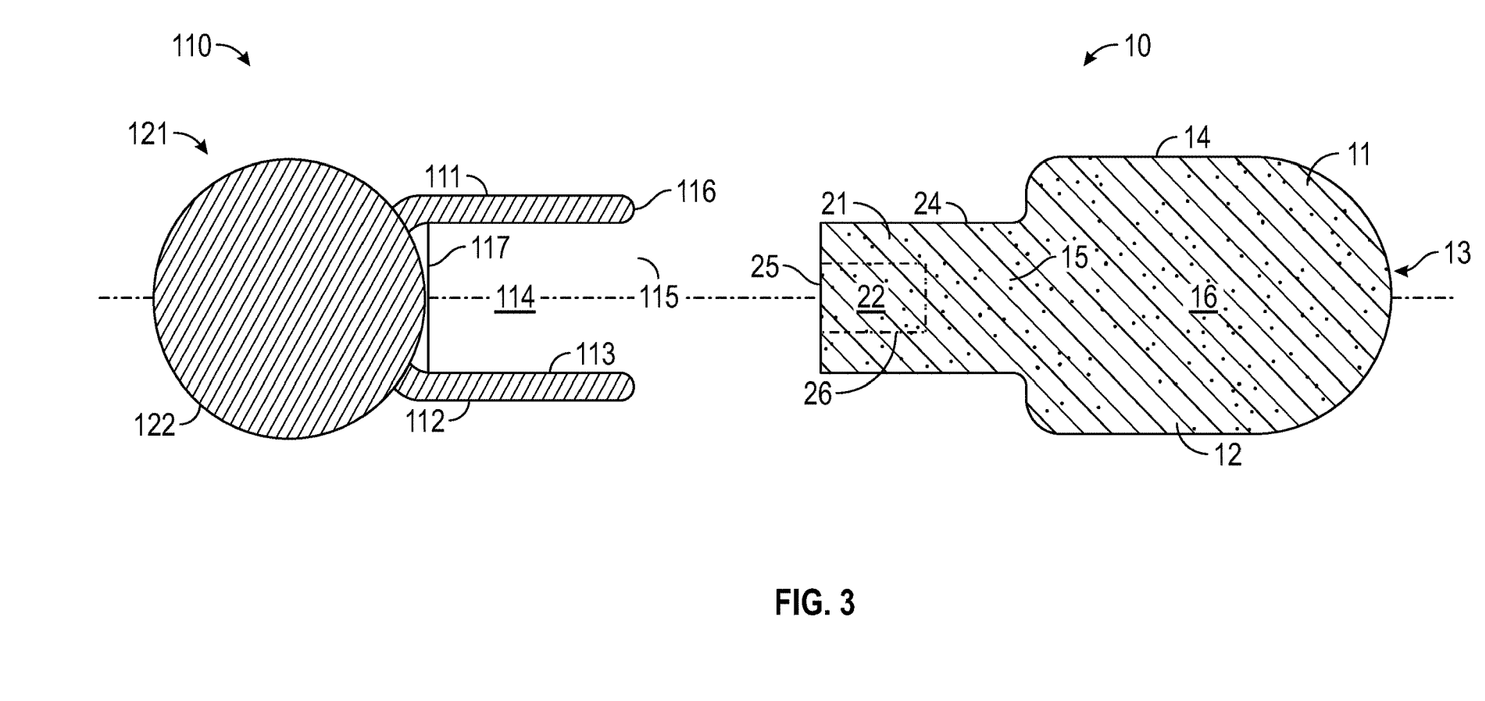
FIG. 3 is a side schematic cross-sectional exploded view of the earplug of FIG. 2.

Disclosed herein is a hearing-protective earplug 1, shown in exemplary embodiment in side view in FIG. 1, in side schematic cross-sectional view in FIG. 2, and in side schematic cross-sectional exploded view in FIG. 3. Earplug 1 comprises a resilient polymeric foam body 10 with a first, forward portion 11 and a second, rearward portion 21 that is integral with the first, forward portion 11. Here and elsewhere herein, integral and like terms refer to items that are of the same chemical composition and that are parts of a single, unitary piece that is made in a single operation (the term integral thus does not encompass parts that are made separately and then joined together). Foam body 10, as provided by first, forward portion 11 and second, rearward portion 21, is at least generally elongate with an identifiable long axis L, a forward end 13, and a rear end 25. (The long axis of foam body 10 will often at least generally coincide with an identifiable long axis of earplug 1 as a whole.)

First, forward portion 11 of foam body 10 comprises an occlusive section 12. Occlusive section 12 is configured to at least substantially fill the cross-sectional area of an ear canal of a human user so as to physically block the passage of airborne sound to provide a desired level of sound attenuation when earplug 1 is inserted into the ear of the user. Forward portion 11 of foam body 10 thus comprises a radially-outward surface 14 which, at least in occlusive section 12 of forward portion 11, conforms to the wall of the ear canal to minimize any leakage of airborne sound between surface 14 and the ear canal wall. In at least some embodiments, at least occlusive section 12 of foam body 10 will be at least generally circular in cross-section when viewed along long axis L of earplug 1. In some embodiments portion 11 of foam body 10 may resemble an elongated cylinder with an arcuate (e.g. at least generally hemispherical) forward end 13.

Earplug 1 comprises a grippable stem 110 that is non-integrally connected to resilient polymeric foam body 10 (in other words, stem 110 and foam body 10 are connected to each other but are not integral with each other). Stem 110 comprises a forward portion 111 and a rearward, grippable portion 121; these portions may often be, but do not necessarily have to be, integral with each other. Rearward grippable portion 121 is configured to be manually gripped by fingers to facilitate the act of inserting earplug 1 into the ear of a user.

Forward portion 111 of stem 110 comprises an annular sleeve 112 that at least partially defines an open-ended cavity 114 that is at least generally front-facing. By open-ended and at least generally front-facing is meant that cavity 114 has at least one open end 115, that faces at least generally toward forward end 13 of foam body 10. Open end 115 of cavity 114 may be defined at least in part by a forwardmost end 116 of stem 110, and in various embodiments may be e.g. at least generally circular in shape, or may be e.g. elliptical, polygonal, or irregular in shape. Cavity 114 may have a closed rear-facing end 117 (as evident in FIGS. 2 and 8), or an open rear-facing end 118 (as evident in FIGS. 7 and 9), as discussed later herein.

By cavity 114 (and open end 115 thereof) being at least generally front-facing, is meant that cavity 114 exhibits an identifiable longitudinal axis that is oriented within plus or minus 30 degrees of a long axis of earplug 1 as a whole and that, when extended beyond the open end of the cavity, extends toward the forward end of earplug 1. In some embodiments cavity 114 may be at least substantially front-facing, meaning that cavity 114 exhibits a longitudinal axis that is oriented within plus or minus 15 degrees of a long axis of earplug 1 as a whole. In some embodiments cavity 114 may be at least essentially front-facing, meaning that cavity 114 exhibits a longitudinal axis that is oriented within plus or minus 5 degrees of a long axis of earplug 1 as a whole. An at least generally front-facing cavity of a stem, as defined and described herein, will be distinguished from, for example, a stem cavity that faces laterally (e.g. radially) outward from a side of a stem in the manner depicted in FIG. 5 of U.S. Pat. No. 6,241,042.

Furthermore, a recess (e.g. a groove, trench, slot, or the like) that is present on a stem and that is not at least partially radially-outwardly-bounded by stem material (for example, a recess in the form of an open-faced elongate groove that extends along a side of a stem), will not be considered to be an at least generally front-facing cavity of a stem as defined herein, regardless of whether a forward end of the recess is e.g. closed, open, or partially open.

In some embodiments, at least about 60, 80, 90, 95, or essentially 100% of radially-outward-facing surface 123 of sleeve 112 of forward portion 111 of stem 110, is an exposed surface. By exposed is meant that such a surface is not radially-outwardly bounded by any foam material of foam body 10. In some embodiments such an exposed surface 123 of stem 110 will provide a locally radially-outwardmost surface of earplug 1. By way of a specific example, in the embodiment of FIGS. 1 and 2, essentially 100% of radially-outward-facing surface 123 is an exposed surface that provides a locally radially-outwardmost surface of earplug 1.

Second, rearward portion 21 of resilient polymeric foam body 10 resides within the open-ended, front-facing cavity 114 that is at least partially defined by annular sleeve 112 of forward portion 111 of stem 110, as most easily seen in the cross-sectional side view of FIG. 2. In various embodiments, rearward portion 21 of foam body 10 may occupy at least about 40, 60, 80, 90, 95, or essentially 100% (as in the exemplary embodiment of FIGS. 2-3) of the volume of cavity 114. In some embodiments, at least a portion of radially-outward surface 24 of second, rearward portion 21 of foam body 10 may be in contact with at least a portion of radially-inward surface 113 of annular sleeve 112, again as shown in FIGS. 2-3.

Sleeve 112 of grippable stem 110 can at least assist in imparting sufficient stiffness to earplug 1 to allow foam body 10 to be inserted at least partially into the ear canal of a human user without foam body 10 unacceptably deflecting (e.g. bending, folding or crumpling) during the insertion process. In some embodiments, this stiffness may be imparted primarily by sleeve 112. In other embodiments, rearward portion 21 of foam body 10 may contribute significantly, e.g. substantially, to the stiffness of earplug 1 (particularly if rearward portion 21 of foam body 10 is densified in comparison to forward portion 11 of foam body 10, as discussed later herein).

The arrangements disclosed herein can thus provide sufficient stiffness to allow earplug 1 to be easily and reliably inserted into a human ear, without necessitating the presence of a stem with a forward portion that is inserted (e.g. embedded) in an open-ended, rear-facing cavity of a rearward portion of a foam body e.g. in the manner disclosed in U.S. Pat. Nos. 5,188,123 and 8,413,663. Thus in various embodiments, second, rearward portion 21 of resilient polymeric foam body 10 of earplug 1 will not comprise any open-ended, at least generally, substantially, or essentially rear-facing, cavity or cavities. (The terms generally, substantially, and essentially rear-facing respectively denote cavities with a longitudinal axis that is oriented within plus or minus 30, 15, or 5 degrees of a long axis of earplug 1 as a whole and that, when extended out beyond the open end of the cavity, extends toward the rearward end of the earplug.) A hypothetical open-ended, rear-facing cavity 26 is shown in phantom lines in FIG. 3, as an example of the type of cavity that is not present in such embodiments. Thus, in some embodiments interior 22 of rearward portion 21 of foam body 10 may be completely free of such cavities (noting that the cells of the foam itself are not to be counted as cavities). In other embodiments, one or more such cavities may be present, but no part of forward portion 111 of stem 110 will reside within, or partially within, any such cavity.

Resilient polymeric foam body 10, including first, forward portion 11 and second, rearward portion 21 that are integral with each other, may be comprised of any suitable polymeric foam. By a polymeric foam is meant a polymeric material that exhibits numerous "empty" (e.g. gas or air-filled) cells. In many embodiments, such a polymeric foam material may be a closed-cell foam in which the majority of cells are each bounded in all directions by solid cell walls of the polymeric material. (It will be appreciated that even in a closed-cell foam some cells may be connected to other cells, owing to statistical fluctuations in any real-world foam production process.) In various embodiments, the polymeric foam material may exhibit a density (measured with the foam in an uncompressed state, unless otherwise specified) of at most about 0.5, 0.4, 0.3, 0.2, 0.15, 0.1, or 0.05 g/cc.

By resilient is meant that the polymeric foam material can be readily manually compressed (e.g. by the fingers of a human user) to a linear compression factor of at least about 30%; and, that upon the release of any such compression, the material will expand to substantially its original dimensions and overall volume, as will be readily understood by an ordinary artisan. In various embodiments, a resilient polymeric foam material may exhibit an instantaneous Shore 00 durometer hardness value of less than 60, 50, 40, or 30 when measured according to the techniques disclosed in U.S. Pat. No. 5,188,123, which is incorporated by reference herein for this purpose.

In some embodiments, resilient polymeric foam body 10 may be comprised of a slow-recovery polymeric foam material. As defined herein, a slow-recovery polymeric foam material is one that exhibits a recovery time of ten seconds or more when tested for recovery properties according to the procedure disclosed in U.S. Pat. No. 7,475,686, which is incorporated by reference herein for this purpose. If foam samples of the appropriate size and configuration are not available for this testing, an ordinary artisan will in many instances be able to identify a slow recovery foam material by a simple semi-quantitative evaluation, e.g. by compressing and releasing a foam portion of an earplug and observing the speed of any subsequent recovery. In various embodiments, a slow-recovery polymeric foam material may exhibit a recovery time of at least about 15, 20, 25, or 30 seconds. In further embodiments, a slow-recovery polymeric foam material may exhibit a recovery time of at most about 5, 4, 3, or 2 minutes, 90 seconds, or 60 seconds. Such a slow-recovery polymeric foam material may be particularly suitable for a compressible or "roll-down" mode of use of earplug 1. It is noted however that an earplug 1 with a foam body 10 that is comprised of a slow-recovery polymeric foam material may be capable of "dual-mode" use such that earplug 1 can be used either in "push-in" mode without any compression of forward portion 11 of foam body 10; or, forward portion 11 can be subjected to at least some manual compression before being inserted into an ear canal.

In some embodiments, resilient polymeric foam body 10 may be comprised of a polymeric foam material that is not a slow-recovery foam material, meaning that the material exhibits a recovery time of less than ten seconds. In various embodiments of this type, the material may exhibit a recovery time of less than about 8, 6, 4, or 2 seconds. Such a foam material may be particularly suitable for a "push-in" mode of use of earplug 1.

All measurements of foam parameters and properties (e.g. recovery time, density, hardness, and so on) will be understood to be performed at room temperature, e.g. at about 21° C. It will be appreciated that a foam body 10 may, depending e.g. on the method of manufacture, exhibit a skin layer that is somewhat densified in comparison to an interior portion of the foam body. In such a case, the interior 16 of foam body 10, e.g. of forward portion 11 of foam body 10, may be used for characterization of the properties of the foam material.

The polymeric foam material of which foam body 10 is comprised may be of any suitable chemical composition. Such compositions may be chosen from e.g. polyurethanes, latex-modified polyurethanes, polyvinylchlorides, polyvinyl acetates, polyolefins, polysiloxanes, acrylic polymers (e.g. polyacrylates, poly(meth)acrylates, and blends and copolymers thereof), and so on. In some embodiments, such compositions may include poly(lactic acid) polymers. In particular embodiments, poly(lactic acid) polymers may be used in combination with one or more other polymers such as e.g. polyvinyl acetates, and/or in combination with plasticizers, e.g. as described in U.S. Provisional Patent Application No. 62/352,633, which is incorporated by reference herein for this purpose. In some embodiments, such compositions may include polyether polyurethanes prepared e.g. from pre-polymers available from Dow Chemical Corporation (Midland Mich.), under the trade designation HYPOL. In particular embodiments, any such polyurethanes may be modified (e.g. blended) with acrylic latexes of the type available from Dow Chemical Corporation under the trade designation UCAR. Further details and attributes of various polymer compositions that may be suitable for inclusion in the polymeric foam material of foam body 10 are disclosed e.g. in U.S. Pat. Nos. 4,158,087, 5,188,123, 5,203,352, 5,650,450, 7,285,576, 7,475,686, and 8,679,607, and in the aforementioned '633 US Provisional Application.

Foam body 10 may be made via any suitable process. For example, a foam precursor material may be injected into a mold cavity so as to form a body with substantially the final form that foam body 10 will have when it is connected to a stem 110 to form earplug 1. Foaming agents or the like may be included so that the thus-formed piece exhibits the desired foam properties (e.g. density, hardness, and so on). In some embodiments a preform may be provided (whether molded in a relatively small piece, or e.g. extruded as a large slab) from which one or more foam bodies 10 may be obtained (e.g. by cutting, punching, or the like), with any excess material being removed if needed (e.g. by trimming, ablating, and so on). In some embodiments a foam body 10 may be produced by extrusion/foaming (followed by separating the solidified extrudate into individual foam bodies).

As noted earlier, earplug 1 comprises a grippable stem 110 that is non-integrally connected to resilient polymeric foam body 10. By this is meant that grippable stem 110 (even if comprised of a material with a similar chemical composition to that of foam body 10) is made separately from foam body 10 and is then connected to foam body 10, rather than stem 110 and foam body 10 being portions of an integral, unitary piece. Stem 110 comprises a forward portion 111 and a rearward, grippable portion 121. Rearward grippable portion 121 may be of any suitable shape, size and configuration that allows a human user to easily grasp portion 121 with fingers. In many embodiments, rearward grippable portion 121 may comprise a "paddle" 122, e.g. a rearmost section that is expanded in one dimension and contracted in a perpendicular dimension in the general manner observable in FIGS. 1-3. In various embodiments, such a paddle may exhibit a width that is greater than a largest outer diameter of the annular sleeve 112 of the forward portion 111 of stem 110 by a factor of at least about 1.2, and/or such a paddle may exhibit a width-to-thickness aspect ratio (measured at the widest point of paddle 122) of at least about 2, 3, 4, 5, or 6. However, such a paddle is not strictly necessary; in fact, stem 110 may be designed such that there is no firm dividing line between rearward, grippable portion 121 of stem 110 and forward, sleeve-bearing portion of stem 110. Rather, in such embodiments a portion of a sleeve 112 may serve as a grippable portion 121, as will be evident e.g. from later discussions of the embodiment depicted in FIG. 10.

The size and shape of various components of stem 110 may be chosen in relation to the size and shape of various components of foam body 10. In various embodiments, stem 110 and foam body 10 may be configured so that an outer diameter of at least occlusive section 12 of first, forward portion 11 of foam body 10 may be greater than a largest outer diameter of annular sleeve 112 of forward portion 111 of stem 110, by a factor of at least about 1.1, 1.2, 1.3, 1.4, 1.6, 1.8, or 2.0.

Figure 4:
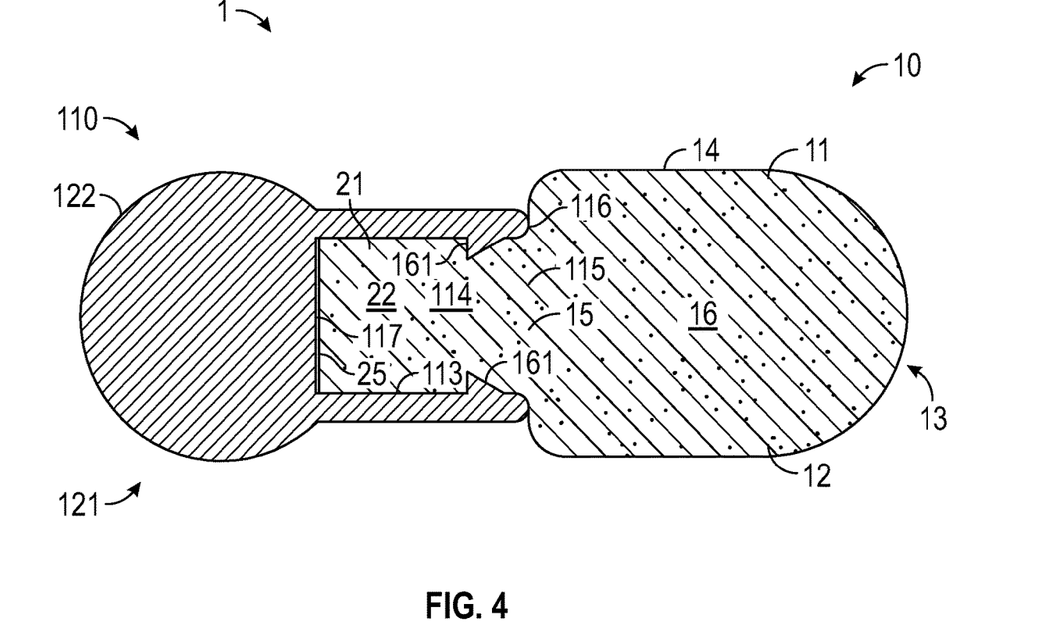
FIG. 4 is a side schematic cross-sectional view of another exemplary earplug.

Stem 110 and components thereof may be made by any suitable process. In some embodiments, stem 110 or portions thereof may be produced by additive methods such as the commonly known 3-D printing. In some embodiments, stem 110 may be at least partially comprised of one or more injection-molded organic polymeric resins. In some embodiments, stem 110 may be an injection-molded unitary body that integrally includes both forward portion 111 and rearward portion 121, e.g. as in FIGS. 1-3. In some embodiments, sleeve 112 of forward portion 111 of an injection-molded stem 110 may comprise one or more protrusions (e.g. barbs) 161 that extend at least generally radially inwardly into the open-ended, front-facing cavity 114 defined by the sleeve, as shown in exemplary embodiment in FIG. 4. In some embodiments, such a protrusion may take the form of a radially-inwardly-protruding flange or lip that extends (whether continuously or discontinuously) around the perimeter of sleeve 112 (e.g. at or near forwardmost end 116 of sleeve 112). Such a protrusion or protrusions may, in finished earplug 1, be at least partially embedded within the second, rearward portion 21 of foam body 10 that resides within cavity 114 of stem 110, and may at least assist in holding stem 110 and foam body 10 connected to each other.

Figure 5:
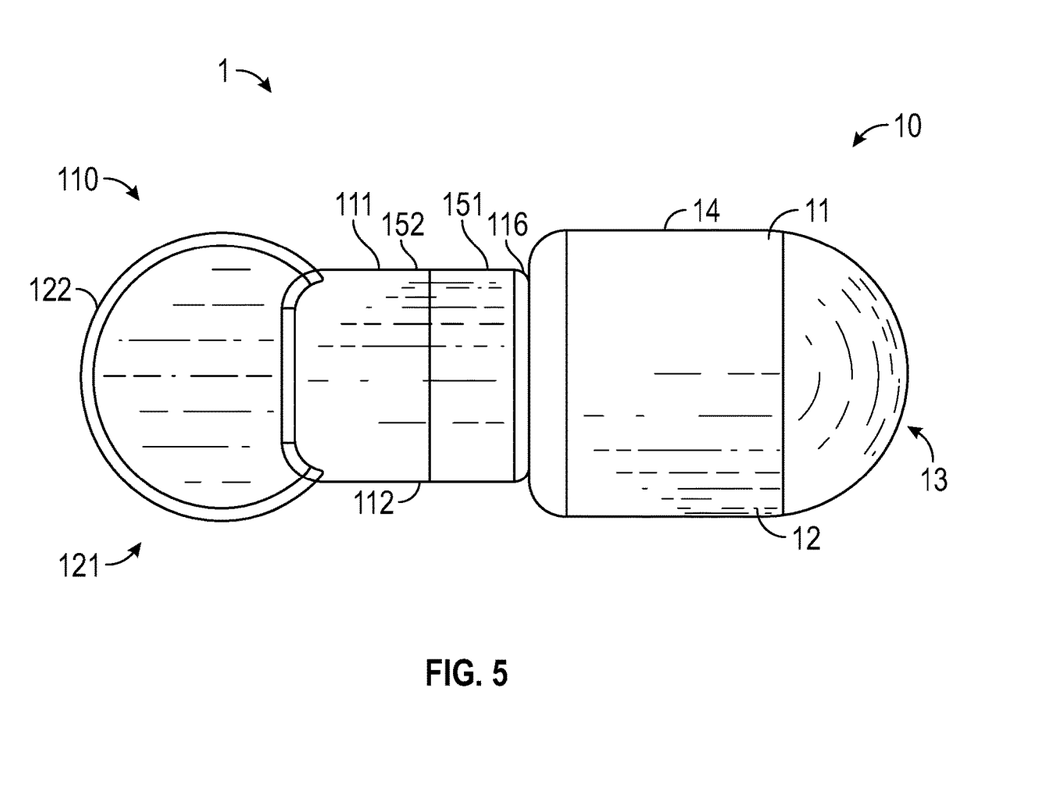
FIG. 5 is a side view of another exemplary earplug.
Figure 6:
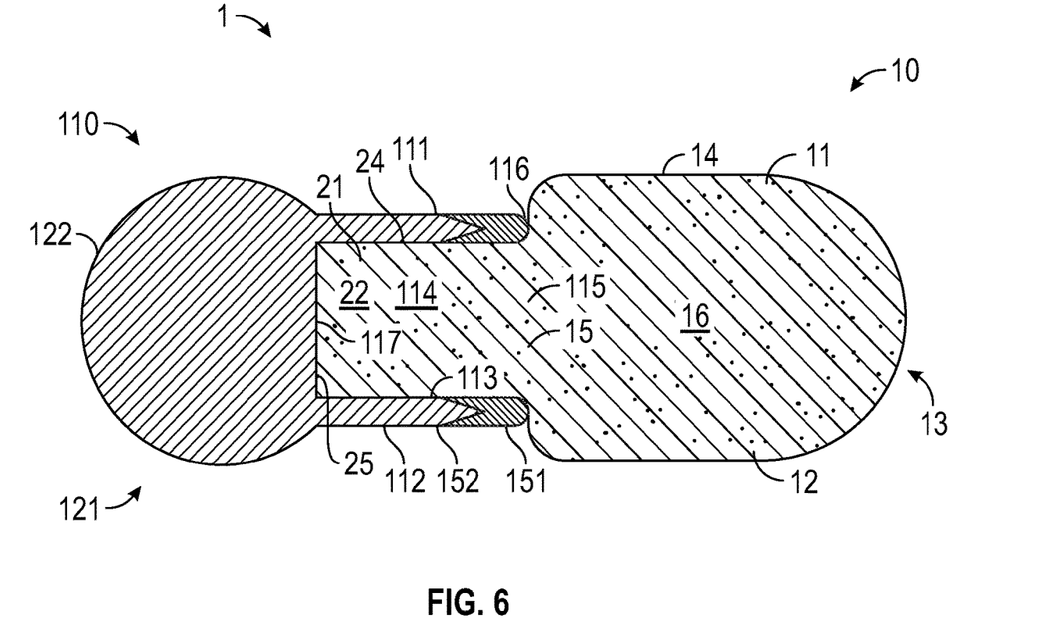
FIG. 6 is a side schematic cross-sectional view of the exemplary earplug of FIG. 5.

In some embodiments, stem 110 may be comprised of first and second components 151 and 152 that are non-disconnectably attached to each other but are not integral with each other. Such components may be configured so that first component 151 provides at least a part of forward portion 111 of stem 110 and second component 152 provides at least a part of rearward, grippable portion 121 of stem 110, as shown in exemplary embodiment in FIGS. 5 and 6. In particular embodiments, first component 151 may provide a forwardmost section (e.g. tip) 116 of stem 110, and second component 152 may provide a rearmost section of stem 110, as in FIGS. 5 and 6. In some embodiments, components 151 and 152 may be injection molded, complementary parts that are fitted together and bonded to each other to form stem 110. Such parts may differ e.g. in any physical property (e.g. modulus, softness, abrasion resistance, and so on) as may be desired to enhance the performance of stem 110. Regardless of the specific configuration, it is emphasized that stem 110 need not be a single, integral piece; for example, a paddle 122 might be separately formed, e.g. of a different material, and then joined to a forward portion to form stem 110. In some embodiments, a stem 110 may be comprised of a second, rearward component 152 that is e.g. an injection-molded piece and that is connected to a foam body 10 by way of a heat-shrink tubing, with the heat-shrink tubing serving as a first, forward component 151 of the thus-formed two-piece stem 110 and with the heat-shrink tubing providing sleeve 112 of stem 110. (Stems that incorporate heat-shrink tubing are discussed in further detail later herein.)

Stem 110 (whether a single unitary part or an assembly of multiple parts) may be comprised of materials of any suitable composition. Suitable materials may be chosen from e.g. metals, composites, and organic polymeric materials such as e.g. injection-molding resins. Potentially suitable injection molding resins may be chosen from e.g. polyamides, polyolefins (e.g. polyethylene, polypropylene, and copolymers and blends thereof), polyacetals, acrylonitrile-butadiene-styrene polymers, ethylene-vinyl acetate copolymers, and so on. In particular embodiments, at least portions of stem 110 may be comprised of material that is a non-foam material, e.g. with a density of at least about 0.7, 0.8, 0.9, or 1.0 g/cc. In various embodiments, at least portions of stem 110 may be comprised of material that exhibits a Shore A Durometer hardness of at least about 10, 20, 40, 60, or 80 (noting that these exemplary densities and hardnesses apply to stems, portions or components thereof made by any method rather than being limited to those made by injection molding.)

Figure 7:
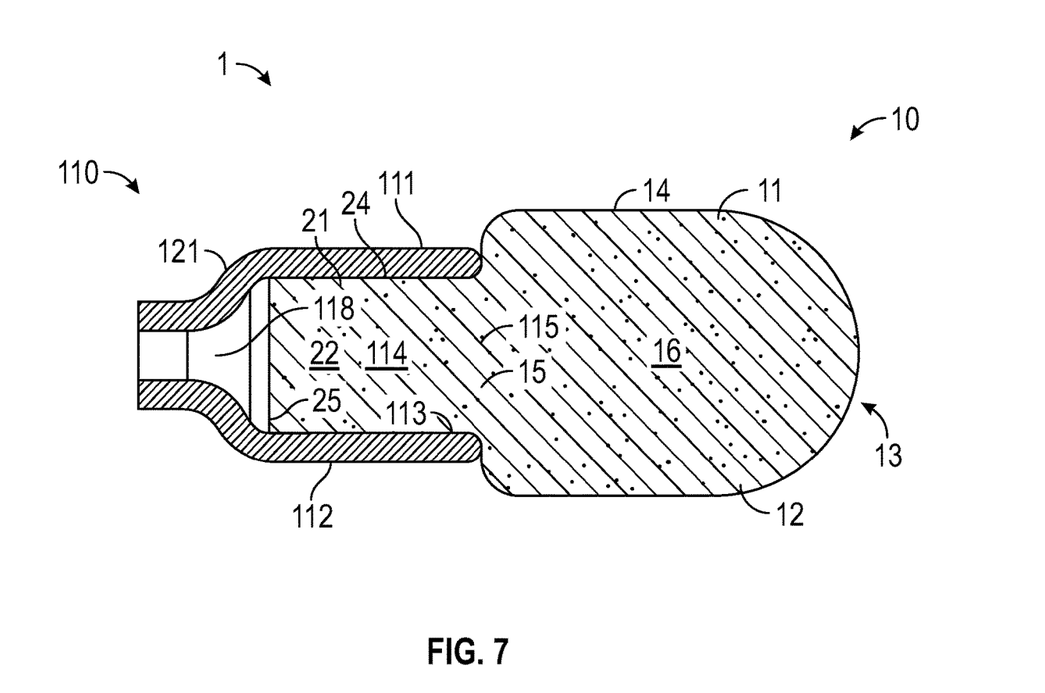
FIG. 7 is a side schematic cross-sectional view of another exemplary earplug.
Figure 8:
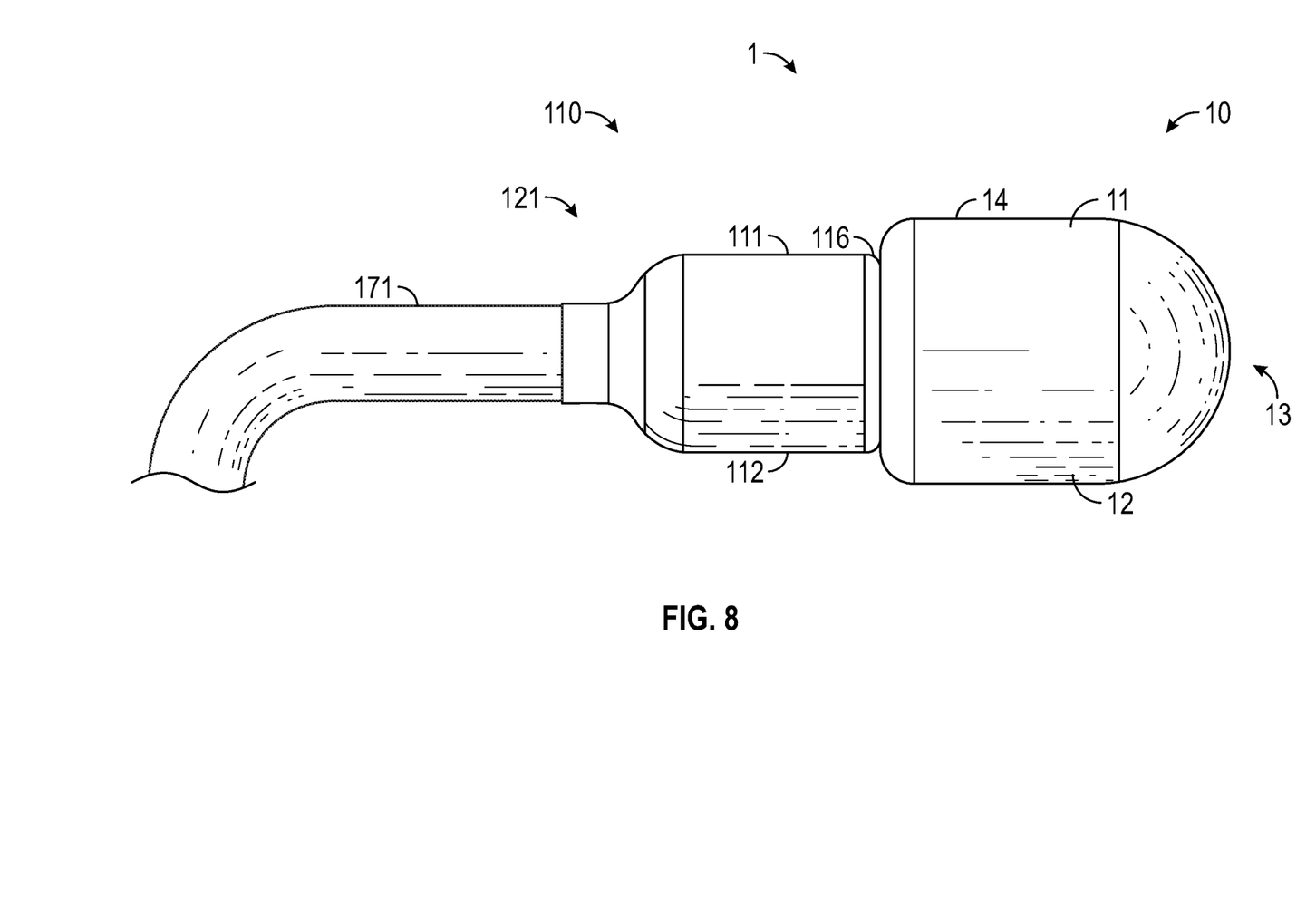
FIG. 8 is a side view of another exemplary earplug comprising a cord.

Stem 110 (whether or not it includes one or more injection-molded parts) may be configured to provide an annular sleeve 112 that at least partially defines an open-ended, front-facing cavity 114, in any suitable way. For example, stem 110 may exhibit a solid wall that defines a closed (dead-end) rear end 117 of cavity 114 so that cavity 114 is an open-ended, front-facing cavity with a closed rear end, as in the exemplary design of FIG. 2. In other embodiments, no such rear solid wall may be present in stem 110, with the result that cavity 114 extends rearwardly to an open rear end 118 of stem 110, as shown in exemplary embodiment in FIG. 7 (noting also that rearward portion 121 as depicted in FIG. 7 does not comprise a paddle as do FIGS. 1-6). In some embodiments, rear end 118 may remain open in finished earplug 1. In other embodiments, a separately-made plug or cap may be inserted or applied to close off the rear end of stem 110. In some embodiments, an end of a cord 171 may be seated into rear end 118 (which may partially, or substantially completely, close off rear end 118 of stem 110), as shown in exemplary embodiment in FIG. 8. It will be appreciated that this is only one exemplary way of connecting a cord to stem 110; if such a cord is desired, it may be joined to stem 110 by any suitable method.

In many embodiments, sleeve 112 and cavity 114 defined thereby may exhibit an at least generally circular cross-section geometry when viewed along long axis L of earplug 1. However, this is not strictly necessary, and sleeve 112 (or at least radially inward-facing surfaces thereof, that define the radially-outward limits of cavity 114) can be any suitable shape, e.g. polygonal (such as e.g. triangular, square, pentagonal, and so on). It is thus emphasized that terms such as annular, radially-inward, radially-outward, diameter, and so on, are used herein for convenience of description and do not require an exactly, or even approximately, circular cross-sectional geometry of sleeve 112 and of cavity 114 defined thereby. For example, in the case of items that are non-circular, an equivalent diameter (e.g. the diameter of a circle with the same area as the non-circular item) may be substituted therefore, for purposes of quantitative characterization.

In some embodiments, cavity 114 as defined e.g. by radially-inward surface 113 of sleeve 112 may be at least slightly elongated in a direction at least generally, substantially, or essentially aligned with a longitudinal axis of earplug 1. In various embodiments, cavity 114 may exhibit an aspect ratio (i.e. a ratio of the elongate length of cavity 114 to a diameter or equivalent diameter of cavity 114) of at least about 1.01, 1.05, 1.1, 1.2, 1.4, 1.6, 2.0, 3.0, or 4.0.

In some embodiments, sleeve 112 may be comprised of a continuously-solid material so that the annular wall of sleeve 112 does not comprise any through-apertures therein. For example, the annular wall of sleeve 112 may be comprised of a solid, injection-molded organic polymeric resin. In other embodiments, at least a portion of sleeve 112 may comprise one or more through-apertures that extend completely through the sleeve wall in an at least generally radially inward-outward direction. In various embodiments, such apertures may take the form of linear or quasi-linear passages (e.g. mechanical perforations, laser-drilled perforations, or track-etched perforations), or may take the form of irregular or tortuous paths. Thus in various embodiments, at least a portion of sleeve 112 may take the form of a netting, a mesh, a woven, non-woven or knitted material, reticulated material, a perforated or microperforated material, a microporous material, or the like. In some embodiments, any such apertures may be sufficiently small that no foam (or foam precursor material) of foam body 10 is able to penetrate therethrough. In some embodiments, such apertures may be sized such that some penetration of e.g. foam precursor material through radially-inward surface 113 of sleeve 112 and into the interior of the annular wall of sleeve 112 may occur. In such cases, some minor penetration of foam precursor material radially outward through the sleeve wall may occur, e.g. so that minor amounts of foam material may occasionally be observed to protrude slightly radially outward beyond radially outer surface 123 of sleeve 112. In such cases, the second, rearward portion 22 of foam body 10 is still considered to reside within open-ended cavity 114 of stem 110.

Stem 110 may be connected to foam body 10 to form earplug 1 in any suitable way. In some embodiments, stem 110 may be non-disconnectably connected to foam body 10, meaning that stem 110 cannot be disconnected from foam body 10 in ordinary use of earplug 1 without unacceptably damaging or destroying earplug 1. In such uses stem 110 will thus remain as a part of earplug 1 after earplug 1 is seated in the ear of a user. In other embodiments, stem 110 may be disconnectably connected to foam body 10 so that it can be disconnected therefrom at a desired time. Such disconnection might be performed by pulling stem 110 rearward, away from foam body 10 (e.g. so that stem 110 and foam body 10 are separated from each other in an arrangement resembling that shown in FIG. 3). In such embodiments, stem 110 may serve as a grippable holder that aids in the insertion of earplug 1 into the ear of a user, with stem 110 then being removed, leaving foam body 10 at least partially in the ear canal to serve as sound-attenuating earplug 1. The strength with which stem 110 is connected to foam body 10, and the force that is thus needed to disconnect the two, can thus be chosen in view of whether stem 110 is to remain with foam body 10 or is to be removed therefrom after insertion of foam body 10 into the ear. If stem 110 is to be disconnectable from foam body 10 in this fashion, foam body 10 may be designed (in particular, the rearward length of rearward portion 21 and the extent to which it protrudes outward from the ear canal of the user) to facilitate removal of foam body 10 from the ear e.g. by grasping rearward portion 21.

In some embodiments, grippable stem 110 may be connected to foam body 10 at least in part by way of a friction fit between radially-outward surface 24 of second, rearward portion 21 of foam body that resides within open-ended, front-facing cavity 114 of forward portion 111 of stem 110, and a radially inward surface 113 of annular sleeve 112 of forward portion 111 of stem 110. In other words, the inner diameter (or equivalent diameter) of sleeve 112 may be chosen in relation to the outer diameter (or equivalent diameter) of rearward portion 21 of foam body 10, to provide a friction fit of any desired holding power. If desired, the outer diameter of rearward portion 21 of foam body 10 may be at least slightly oversized in relation to the inner diameter of sleeve 112, so that portion 21 is at least slightly compressed when fitted within cavity 114, to achieve the desired friction fit. As noted previously, one or more protrusions may protrude radially inward from sleeve 112 of forward portion 111 of stem 110 to enhance the connecting of stem 110 to foam body 10. In some embodiments, grippable stem 110 may be connected to foam body 10 at least in part by way of adhesive bonding of at least a part of forward portion 111 of stem 110, to at least a part of rearward portion 21 of foam body 10. Such adhesive bonding might be achieved by use of e.g. a pressure-sensitive adhesive, a photocurable adhesive, glue, rubber cement, and so on. Other bonding methods such as solvent welding and ultrasonic welding can be contemplated. In general, any suitable method or combination of methods may be used, whether such methods are e.g. adhesive, mechanical, or thermal in nature. Any such methods of connecting and/or bonding may be used in combination as desired.

In various embodiments, foam body 10 may be produced (e.g. by forming of a foam in-situ from a precursor material within a cavity of a mold, by cutting material away from a preform, etc.), stem 110 may be produced (e.g. by injection-molding of a suitable thermoplastic molding resin), and the two may then be brought together in any suitable manner. For example, the two items may be formed separately and then brought together to form earplug 1. Rearward portion 21 of foam body 10 may be shaped and/or sized, and/or stem 110 may be pushed onto rearward portion 21 of foam body 10 to any desired extent, to provide that rearward portion 21 of foam body 10 fills the volume of open-ended, front-facing cavity 114 of stem 110, to any desired extent.

Figure 9:
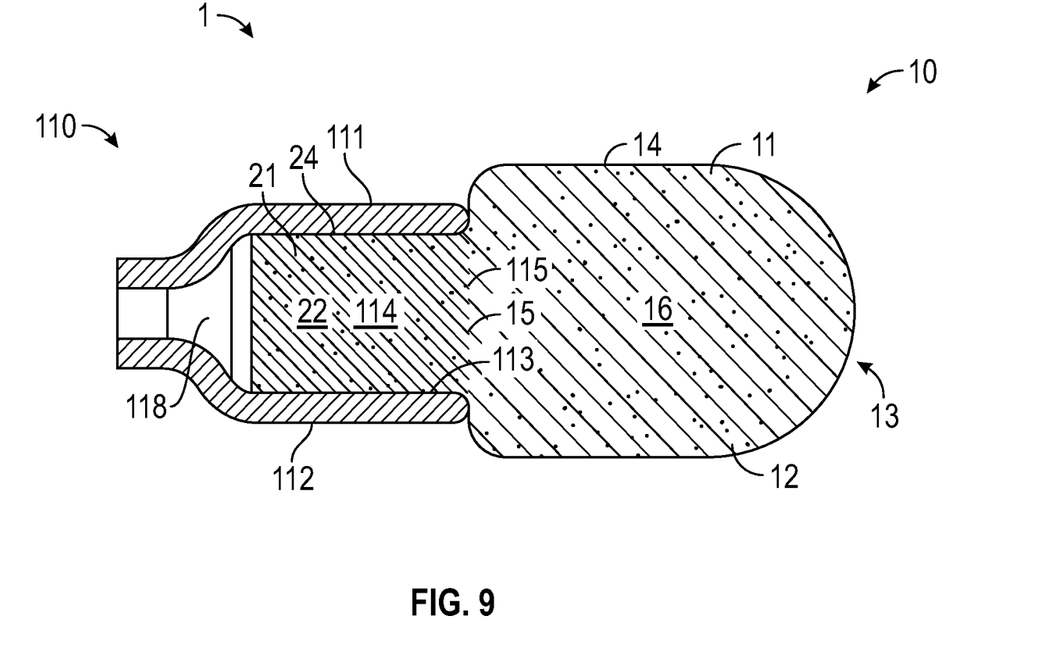
FIG. 9 is a side schematic cross-sectional view of another exemplary earplug.
Figure 10:
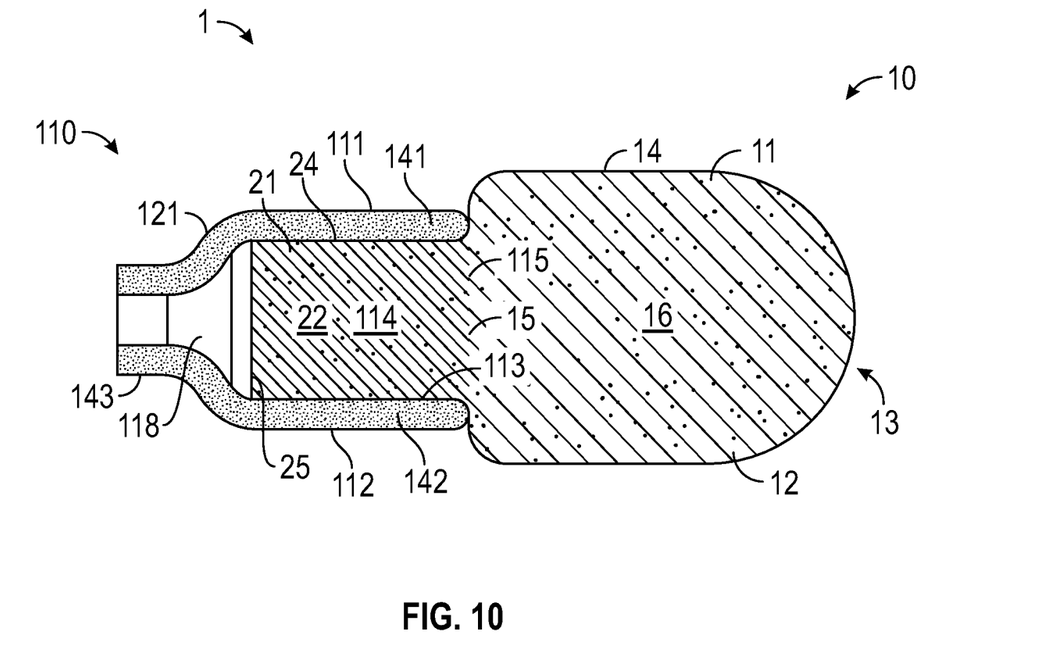
FIG. 10 is a side schematic cross-sectional view of another exemplary earplug.

In some embodiments, rearward portion 21 of foam body 10 may be disposed within cavity 114 with little or no compression of portion 21. In such cases, the density of first, forward portion 11 of foam body 10 may be quite similar to (e.g., within 95-105% of) that of second, rearward portion 21 of foam body 10. In other embodiments, portion 21 may be compressed (e.g. reversibly or irreversibly compressed) to a desired extent prior to being disposed within cavity 114, as in the exemplary embodiment depicted in FIG. 9. In various embodiments, portion 21 may be compressed to a volumetric compression ratio of about 0.9, 0.8, 0.6, 0.4, or 0.2 (noting that a volumetric compression ratio of, for example, 0.8 means that the volume of portion 21 as compressed, is approximately 80% of the volume of portion 21 in its previous, uncompressed condition, and further noting that a "lower" compression ratio denotes a smaller value of the compression ratio, i.e. denotes a more highly compressed foam). In such cases, portion 21 may be restrained from expanding to its original condition, by radially-inward wall surfaces 113 of sleeve 112, as shown in exemplary embodiment in FIG. 9. In such cases, a transition in foam density may provide a readily identifiable boundary 15 between forward portion 11 and rearward portion 21, as indicated in FIGS. 9 and 10. (In embodiments in which portion 21 of foam body 10 is not compressed, no such transition and boundary in the density of the foam material may be evident.) It will be appreciated that in embodiments in which stem 110 is disconnectable from foam body 10 (so as to put these items into a separated configuration similar to that depicted in FIG. 3) and in which portion 21 is reversibly compressed within cavity 114, any disconnecting of stem 110 from foam body 10 may result in rearward portion 21 of foam body 10 (formerly restrained from expanding by sleeve 112) expanding e.g. so as to exhibit a similar diameter to that of forward portion 11.

In some embodiments, earplug 1 may be an insert-molded earplug, achieved e.g. by positioning a previously-made stem 110 as an insert within a molding cavity of an injection-molding apparatus, and then injecting a precursor material of foam body 10 into the cavity so that a first portion of the material at least partially fills cavity 114 defined by sleeve 112 of stem 110, and so that a second portion of the material fills a portion of the molding cavity to form forward portion 11 of foam body 10. The first and second portions thus respectively provide rearward and forward portions of the thus-produced foam body, with the rearward portion being disposed, as formed in-situ, within cavity 114 of stem 110. In an alternative approach, earplug 1 may be formed by positioning a previously-made foam body 10 as an insert within a molding cavity, and then injecting a precursor material of stem 110 (e.g. a molten thermoplastic molding resin) into the cavity so that a portion of the material at least partially flows around a rearward portion 21 of the foam body 10 to form sleeve 112, and a remaining portion of the molten material fills a portion of the molding cavity so as to form any remaining portions (e.g. a grippable rear portion or paddle) of stem 110.

Although the discussions above have primarily focused on a grippable stem 110 that is comprised of one or more injection-molded parts, in general a stem 110 can be provided in any desired manner, made of any suitable material. In some embodiments, at least a sleeve 112 of stem 110 can be comprised of heat-shrink tubing (as used herein, the term heat-shrink tubing refers to a heat-shrinkable tubing material that has been subjected to heat-shrinking process that caused the tubing to shrink at least generally radially inward from a first, larger diameter, to a second, significantly smaller diameter.)

An exemplary earplug 1 comprising a stem 110 provided by heat-shrink tubing 141 is shown in exemplary embodiment in FIG. 10. Such an earplug may be provided e.g. by slipping a forward section 142 of a heat-shrinkable tubing onto a rearward portion 21 of a foam body 10, and then subjected at least the forward section 142 of the tubing to a temperature sufficiently high to cause at least forward section 142 of the tubing to shrink radially inward. It will be appreciated that such a process may (depending e.g. on the magnitude of the reduction in the inner diameter of the tubing, and depending also on the compressibility of the polymeric foam material of rearward portion 21 of foam body 10) cause a slight, significant, or substantial reduction in the outer diameter of portion 21 of foam body 10 and a commensurate increase in the density of portion 21 of foam body 10. In other words, in some cases the heat-shrink tubing may shrink tightly around portion 21 of foam body 10 and may densify portion 21 in comparison to the density of forward portion 11 of foam body 10. In various embodiments of this type forward portion 11 of foam body 10 may exhibit a density that is no greater than about 90, 80, or 70% of the density exhibited by rearward portion 21 of foam body 10.

Figure 11:
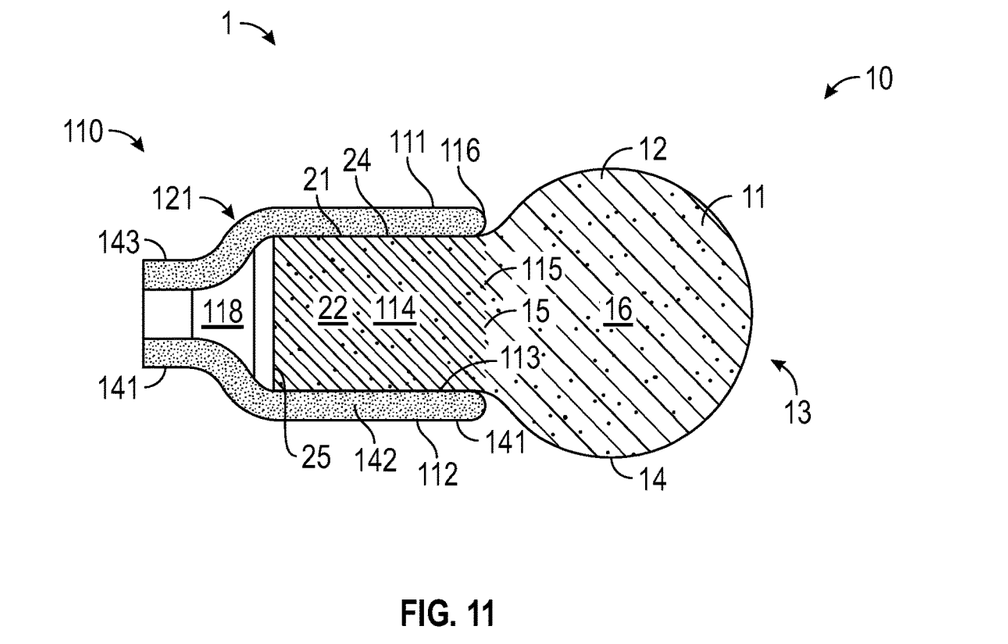
FIG. 11 is a side schematic cross-sectional view of another exemplary earplug.

FIG. 11 depicts another exemplary earplug 1 in which a stem 110 is provided by heat-shrink tubing, but with differences from the earplugs of FIGS. 1-10. Forward portions 11 of foam bodies 10 as depicted in FIGS. 1-10 all exhibit a generally cylindrical appearance with an outer diameter that varies at most slightly along the long axis L of foam body 10 (at least until nearing forward end 13 of foam body 10). In such embodiments, any area, or multiple areas, along long axis L of foam body 10 may serve as an occlusive section 12 (depending e.g. on the depth to which foam body 10 is inserted in the ear canal). FIG. 11 is an example of an alternative design, in which (due e.g. to the shape of forward portion 11 of foam body 10 as made, and/or due to at least some compression of the rear section of forward portion 11 as a result of shrinkage of heat-shrink tubing 141) forward portion 11 of foam body 10 exhibits a rounded shape in which the cross-sectional area of portion 11 rises to a maximum, and then falls, along the long axis L of portion L. In such embodiments, one particular section of forward portion 10 exhibits a largest diameter and thus will typically serve as occlusive section 12 of foam body 10, as denoted in FIG. 11. (It will be understood that foam bodies 10 of this general type are not limited to use with earplugs in which the sleeve and/or entirety of the stem is provided by heat-shrink tubing.)

In the embodiment of FIGS. 10 and 11, the heat-shrink tubing 141 was provided at a length longer than that of rearward portion 21 of foam body 10, thus in the finished earplug a rear section 143 of the heat-shrink tubing extends rearwardly to provide a rearmost section of stem 110. In the embodiments of FIGS. 10 and 11, rearmost section 143 of the heat-shrink tubing exhibits a smaller diameter than forward section 142 of the heat-shrink tubing, since greater shrinking was able to occur due to the absence of any foam material within this part of the tubing. It will be understood that the magnitude of any such additional shrinkage may depend e.g. on the properties of the foam material and of the heat-shrinkable tubing, and/or on the aggressiveness of the heat-shrink process. In some embodiments the heat-shrinkable tubing may be provided with a length that is at least substantially similar to that of rearward portion 21 of foam body 10, which may produce a finished earplug 1 at least somewhat resembling the earplug of FIG. 12. The rear end of a stem 110 formed of heat-shrink tubing may remain open as shown in FIGS. 10-11; or, it may be e.g. plugged with a cap or may have an end of a cord seated thereinto.

Rather than a sleeve 112 of stem 110 being provided by an injection-molded part or by a heat-shrink tubing, in some embodiments sleeve 112 of stem 110, and in some cases the entirety of stem 110, may be provided by spiral-wrapping a sheet-like layer around a rearward portion 21 of a foam body 10. By spiral-wrapping is meant wrapping the sheet-like layer continually circumferentially around portion 21 of the foam body until multiple (e.g., 2, 3, 4, 5 or more) concentrically-overlapping layers of the sheet-like material build up radially atop each other to form a sleeve comprising a multilayer stack of layers of the sheet-like material. It may be convenient that the sheet-like material is self-adherent; in one example, the sheet-like layer may be a length of adhesive tape with a pressure-sensitive adhesive on one major surface and that exhibits suitable width and length to be wrapped around rearward portion 21 of foam body 10.

In some embodiments rearward portion 21 of foam body 10 may be compressed and maintained in compressed condition during the wrapping process, with the result that in the finished earplug, rearward portion 21 may exhibit a significantly higher density than forward portion 11. In other embodiments, no such compressing may be performed, so that in the finished earplug the density of rearward portion 21 is very similar to that of forward portion 11.

Figure 12:
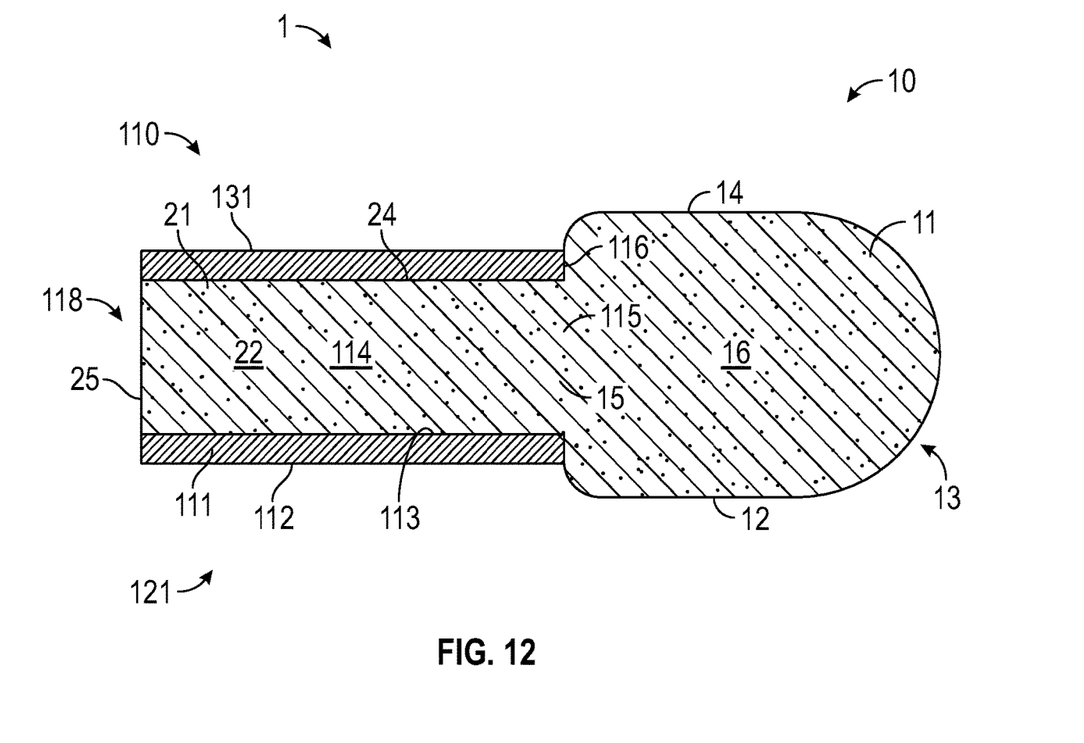
FIG. 12 is a side schematic cross-sectional view of another exemplary earplug.

If the width of the sheet-like material is selected to closely match the forward-rearward length of rearward portion 21 of the foam body 10, the finished earplug may take the general form presented in exemplary embodiment in FIG. 12, in which sleeve 112, forward portion 111, and in fact the entirety of stem 110, is provided by a spiral-wrapped sheet-like material (e.g. an adhesive tape) 131. It is emphasized however that FIG. 12 is an exemplary depiction and that such a spiral-wrapped sheet-like material can have any desired configuration (e.g. width) and can e.g. extend rearward past the rear end 25 of rearward portion 21 of foam body 10. In some embodiments, a separate item (e.g. a molded piece) may provide a rearward portion of stem 110; in such cases the item may be e.g. positioned closely rearward of rear end 25 of foam body 10 and e.g. an adhesive tape may be positioned so that its width partially overlaps both a forward section of the item and at least a rearmost section of rearward portion 21 of foam body 10. The tape may then be spiral-wrapped about the respective sections of foam body 10 and the item, to provide a two-piece stem in which the spiral-wrapped tape provides the sleeve and the item provides the rearward portion of the stem.

However produced and regardless of the variation in specific design and components discussed above, an earplug 1 may be configured and used in any desired manner. As noted, in some embodiments earplug 1 may comprise a cord 171. Two earplugs 1 thus may be supplied to a user, as a pair of earplugs connected to each other by way of a cord that is connected e.g. to the stem of each earplug. In some embodiments, a user may be supplied with a kit comprising at least one hearing-protective earplug 1 (whether packaged as a one or more single earplugs, one or more pairs of non-corded earplugs, or as one or more pairs of corded earplugs) along with instructions for use of the earplug(s).

As noted earlier, earplug 1 as disclosed herein may be configured to be insertable into an ear in a compressible ("roll-down"), and/or in a "push-in" mode. That is, in some embodiments sleeve 112 (possibly aided by rearward portion 21 of foam body 10) may provide sufficient stiffness to allow forward portion 11 of foam body 10 to be inserted at least partially into the ear canal of a user without the need to compress (i.e. "roll down") forward portion 11. However, should a user desire it (e.g. if the ear is particularly small and/or tortuous), and if foam body 10 comprises a slow-recovery foam composition, forward portion 11 may be compressed to some degree prior to insertion.

Thus, in some embodiments, instructions provided with earplug 1 (e.g. along with a kit including at least one earplug 1) may include a procedure for manually compressing the first, forward portion 11 of the resilient polymeric foam body 10 and then inserting the earplug into an ear of a human user while the first, forward portion 11 of the resilient polymeric foam body 10 is still in an at least partially compressed condition. In other embodiments such instructions may include a step of inserting earplug 1 into an ear canal of a human user without including a prior step of manually compressing the first, forward portion 11 of the resilient polymeric foam body 10 of the earplug. In some embodiments, instructions for using either procedure, depending on the user's choice, may be included.

It has been found that the ease with which the entry of at least forward portion 11 of resilient polymeric foam body 10 into a human ear canal may be enhanced by way of foam body 10 being rotated about an axis at least generally coincident with long axis L of earplug 1, at least during the initial entry of forward end 13 of foam body 10 into the ear canal. This being the case, in some embodiments instructions provided with earplug 1 may include a step of rotating the earplug about a rotation axis that is at least generally aligned with a long axis of the earplug, during at least a part of a time during which the earplug is being moved forward so as to enter the ear canal of the user.

Instructions for use of earplug(s) 1 may accompany the earplug (e.g. so that the instructions and the at least one earplug collectively form a kit) in any suitable manner. In some embodiments, such instructions may be printed on a paper insert that accompanies the earplug. In some embodiments, such instructions may be printed on the packaging that an individual earplug, or a pair of earplugs, is packaged in. In some embodiments, such instructions may be provided as an insert, or printed on the packaging, of a container containing multiple (e.g., 4, 8, 16, 32 or more) bulk-packaged earplugs. In some embodiments, such instructions may be virtual instructions that are provided on a web site (e.g. in pdf format or html format), with a link to the web site being provided in accompaniment with earplug 1. All such modes of providing instructions to an end user are encompassed by the herein-described concept of supplying a kit comprising at least one earplug 1, along with instructions for use of the earplug, to a user.

LIST OF EXEMPLARY EMBODIMENTS

Embodiment 1 is a hearing-protective earplug, comprising: a resilient polymeric foam body that comprises a first, forward portion that comprises an occlusive section, and a second, rearward portion that is integral with the first, forward portion, and, a grippable stem that is non-integrally connected to the resilient polymeric foam body and that comprises a forward portion and a rearward, grippable portion; wherein at least the forward portion of the stem comprises an annular sleeve that at least partially defines an open-ended, at least generally front-facing cavity,
and wherein the second, rearward portion of the resilient polymeric foam body resides within the open-ended, at least generally front-facing cavity of the forward portion of the stem.

Embodiment 2 is the hearing-protective earplug of embodiment 1 wherein at least the second, rearward portion of the resilient polymeric foam body does not comprise any open-ended, at least generally rear-facing cavity or cavities within which any part of the forward portion of the stem resides.

Embodiment 3 is the hearing-protective earplug of embodiment 1 wherein at least the second, rearward portion of the resilient polymeric foam body does not comprise any open-ended, at least substantially rear-facing cavity or cavities.

Embodiment 4 is the hearing-protective earplug of any of embodiments 1-3 wherein the open-ended, at least generally front-facing cavity that is defined by the annular sleeve is an at least substantially front-facing, elongated cavity that exhibits an aspect ratio of at least about 1.4 and that is open-ended at a forward end of the sleeve and closed-ended toward a rearward end of the sleeve.

Embodiment 5 is the hearing-protective earplug of any of embodiments 1-4 wherein the stem is at least partially comprised of an injection-molded organic polymeric resin that is a non-foam material with a density of at least about 0.7 g/cc.

Embodiment 6 is the hearing-protective earplug of embodiment 5 wherein the forward portion of the grippable stem and the rearward, grippable portion of the grippable stem, are integral portions of a unitary, injection molded part.

Embodiment 7 is the hearing-protective earplug of any of embodiments 1-5 wherein at least the forward portion of the stem is comprised of heat-shrink tubing.

Embodiment 8 is the hearing-protective earplug of any of embodiments 1-5 wherein at least the forward portion of the stem is at least partially comprised of a sheet-like material that is spiral-wrapped around the second, rearward portion of the resilient polymeric foam body to form at least the annular sleeve of the forward portion of the stem.

Embodiment 9 is the hearing-protective earplug of any of embodiments 1-5 and 7-8 wherein the stem is comprised of first and second components that are non-disconnectably attached to each other but are not integral with each other, and that are configured so that the first component provides at least a part of the forward portion of the stem and the second component provides at least a part of the rearward, grippable portion of the stem.

Embodiment 10 is the hearing-protective earplug of any of embodiments 1-9 wherein the rearward, grippable portion of the stem includes a grippable paddle that exhibits a width-to-thickness aspect ratio of at least about 4.

Embodiment 11 is the hearing-protective earplug of any of embodiments 1-10 wherein at least the occlusive section of the resilient polymeric foam body is comprised of a slow-recovery organic polymeric foam material.

Embodiment 12 is the hearing-protective earplug of any of embodiments 1-11 wherein the entirety of the resilient polymeric foam body is an organic polymeric foam material that is not a slow-recovery foam material.

Embodiment 13 is the hearing-protective earplug of any of embodiments 1-12 wherein the first, forward portion of the resilient polymeric foam body exhibits a density that is at least about 95% of a density exhibited by the second, rearward portion of the resilient polymeric foam body that resides within the open-ended, front-facing cavity of the forward portion of the stem.

Embodiment 14 is the hearing-protective earplug of any of embodiments 1-12 wherein the second, rearward portion of the resilient polymeric foam body that resides within the open-ended, front-facing cavity of the forward portion of the stem, is compressed to a volumetric compression ratio of about 0.6 or lower.

Embodiment 15 is the hearing-protective earplug of any of embodiments 1-14 wherein an outer diameter of at least the occlusive section of the first, forward portion of the resilient polymeric foam body is greater than a largest outer diameter of the annular sleeve of the forward portion of the stem, by a factor of at least about 1.2.

Embodiment 16 is the hearing-protective earplug of any of embodiments 1-15 wherein the resilient polymeric foam body is comprised of a material selected from the group consisting of polyurethane foams, polyvinyl chloride foams, polyolefin foams, polylactic acid foams, acrylic foams, and polysiloxane foams.

Embodiment 17 is the hearing-protective earplug of any of embodiments 1-16 wherein the grippable stem is disconnectably connected to the resilient polymeric foam body.

Embodiment 18 is the hearing-protective earplug of any of embodiments 1-16 wherein the grippable stem is non-disconnectably connected to the resilient polymeric foam body.

Embodiment 19 is the hearing-protective earplug of any of embodiments 1-18 wherein the grippable stem is connected to the resilient polymeric foam body at least in part by way of a friction fit between a radially outward surface of the second, rearward portion of the resilient polymeric foam body that resides within the open-ended, front-facing cavity of the forward portion of the stem, and a radially inward surface of the annular sleeve of the forward portion of the stem.

Embodiment 20 is the hearing-protective earplug of any of embodiments 1-19 wherein the grippable stem is connected to the resilient polymeric foam body at least in part by way of adhesive bonding of a surface area of the stem to a surface area of the resilient polymeric foam body.

Embodiment 21 is the hearing-protective earplug of any of embodiments 1-20 wherein the annular sleeve of the forward portion of the stem comprises at least one protrusion that extends at least generally radially inwardly into the open-ended, front-facing cavity defined by the sleeve and that is at least partially embedded within the second, rearward portion of the resilient polymeric foam body that resides within the open-ended, front-facing cavity defined by the sleeve.

Embodiment 22 is the hearing-protective earplug of any of embodiments 1-6 and 9-21 wherein the hearing-protective earplug is an insert-molded earplug.

Embodiment 23 is a hearing-protective product comprising first and second hearing-protective earplugs of any of embodiments 1-22, the first earplug being connected to the second earplug by a cord, one end of which is connected to the grippable stem of the first earplug and a second, opposing end of which is connected to the grippable stem of the second earplug.

Embodiment 24 is a kit comprising at least one hearing-protective earplug of any of embodiments 1-11 and 13-23 along with instructions for use of the earplug, which instructions include a procedure for manually compressing the first, forward portion of the resilient polymeric foam body and then inserting the earplug into an ear of a human user while the first, forward portion of the resilient polymeric foam body is still in an at least partially compressed condition.

Embodiment 25 is a kit comprising at least one hearing-protective earplug of any of embodiments 1-23 along with instructions for use of the earplug, which instructions include a step of inserting the earplug into an ear canal of a human user without being preceded by a step of manually compressing the first, forward portion of the resilient polymeric foam body.

Embodiment 26 is a kit comprising at least one hearing-protective earplug of any of embodiments 1-23 along with instructions for use of the earplug, which instructions include a step of rotating the earplug about a rotation axis that is at least generally aligned with a long axis of the earplug, during at least a part of a time during which the earplug is being moved forward so as to be inserted into an ear canal of the user.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document that is incorporated by reference herein but to which no priority is claimed, this specification as written will control.

What is claimed is:

1. A hearing-protective earplug, comprising:
a resilient polymeric foam body that comprises a first, forward portion that comprises an occlusive section, and a second, rearward portion that is integral with the first, forward portion,
and,
a grippable stem that is non-integrally connected to the resilient polymeric foam body and that comprises a forward portion and a rearward, grippable portion;
wherein at least the forward portion of the grippable stem comprises an annular sleeve that at least partially defines an open-ended, front-facing cavity,
wherein the second, rearward portion of the resilient polymeric foam body resides within the open-ended, front-facing cavity of the forward portion of the grippable stem;
and wherein at least the second, rearward portion of the resilient polymeric foam body does not comprise any open-ended, at least substantially rear-facing cavity or cavities.

2. The hearing-protective earplug of claim 1 wherein the open-ended, front-facing cavity is an open-ended, front facing elongated cavity front-facing, elongated cavity.

3. The hearing-protective earplug of claim 1 wherein at least the occlusive section of the resilient polymeric foam body is comprised of a slow-recovery organic polymeric foam material.

4. The hearing-protective earplug of claim 1 wherein the entirety of the resilient polymeric foam body is an organic polymeric foam material that is not a slow-recovery foam material.

5. The hearing-protective earplug of claim 1 wherein the first, forward portion of the resilient polymeric foam body exhibits a density that is from 95% to 105% of a density exhibited by the second, rearward portion of the resilient polymeric foam body.

6. The hearing-protective earplug of claim 1 wherein the second, rearward portion of the resilient polymeric foam body is compressed to a volumetric compression ratio from 0.6 to 0.2.

7. The hearing-protective earplug of claim 1 wherein the resilient polymeric foam body is comprised of a material selected from the group consisting of polyurethane foams, polyvinyl chloride foams, polyolefin foams, poly(lactic acid) foams, acrylic foams, and polysiloxane foams.

8. The hearing-protective earplug of claim 1 wherein the grippable stem is disconnectably connected to the resilient polymeric foam body.

9. The hearing-protective earplug of claim 1 wherein the grippable stem is connected to the resilient polymeric foam body at least in part by way of a friction fit between a radially outward surface of the second, rearward portion of the resilient polymeric foam body that resides within the open-ended, front-facing cavity of the forward portion of the grippable stem.

10. The hearing-protective earplug of claim 1 wherein the grippable stem is connected to the resilient polymeric foam body at least in part by way of adhesive bonding of a surface area of the grippable stem to a surface area of the resilient polymeric foam body.

11. The hearing-protective earplug of claim 1 wherein the annular sleeve of the forward portion of the grippable stem comprises at least one protrusion that extends at least generally radially inwardly into the open-ended, front-facing cavity defined by the annular sleeve and that is at least partially embedded within the second, rearward portion of the resilient polymeric foam body.

12. A hearing-protective product comprising first and second hearing-protective earplugs of claim 1, the first earplug being connected to the second earplug by a cord, one end of which is connected to the grippable stem of the first earplug and a second, opposing end of which is connected to the grippable stem of the second earplug.

13. A kit comprising at least one hearing-protective earplug of claim 1 along with instructions for use of the earplug, which instructions include a procedure for manually compressing the first, forward portion of the resilient polymeric foam body and then inserting the earplug into an ear of a human user while the first, forward portion of the resilient polymeric foam body is still in an at least partially compressed condition.

14. A kit comprising at least one hearing-protective earplug of claim 1 along with instructions for use of the earplug, which instructions include a step of inserting the earplug into an ear canal of a human user without being preceded by a step of manually compressing the first, forward portion of the resilient polymeric foam body.

15. A kit comprising at least one hearing-protective earplug of claim 1 along with instructions for use of the earplug, which instructions include a step of rotating the earplug about a rotation axis that is at least generally aligned with a long axis of the earplug, during at least a part of a time during which the earplug is being moved forward so as to be inserted into an ear canal of the user.

* * * * *

UNITED STATES PATENT AND TRADEMARK OFFICE
CERTIFICATE OF CORRECTION

PATENT NO. : 11,173,069 B2
APPLICATION NO. : 16/471844
DATED : November 16, 2021
INVENTOR(S) : Cait Meree It is certified that error appears in the above-identified patent and that said Letters Patent is hereby corrected as shown below:

In the Claims

Column 17
Line 23, In Claim 2, after "open-ended,", delete "front facing elongated cavity".
Line 40, In Claim 6, delete "body" and insert -- body, --, therefor.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*